(12) United States Patent
Wiederin et al.

(10) Patent No.: US 8,551,401 B1
(45) Date of Patent: Oct. 8, 2013

(54) SAMPLE PREPARATION ASSEMBLY

(75) Inventors: Daniel R. Wiederin, Omaha, NE (US); Gary Barrett, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 415 days.

(21) Appl. No.: 12/778,449

(22) Filed: May 12, 2010

(51) Int. Cl.
*G01N 33/00* (2006.01)
(52) U.S. Cl.
USPC ................ 422/54; 422/400; 422/83
(58) Field of Classification Search
USPC .............................. 422/54, 400, 83
See application file for complete search history.

(56) References Cited

U.S. PATENT DOCUMENTS

2008/0173810 A1* 7/2008 Morrisroe ............. 250/288
2011/0024615 A1* 2/2011 Tanner et al. ............. 250/282

* cited by examiner

*Primary Examiner* — Sam P Siefke
(74) *Attorney, Agent, or Firm* — Advent, LLP

(57) ABSTRACT

A sample preparation assembly includes a torch configured for use with an inductively coupled plasma spectroscopy instrument. The torch includes at least two approximately cylindrical tubes arranged substantially concentrically. The sample preparation assembly also includes an injector configured for use with the inductively coupled plasma spectroscopy instrument. The injector includes an injection nozzle and a spray chamber. The sample preparation assembly further includes a heat sink element. The heat sink element includes a securing element. The securing element is configured to mate with a mounting element of the torch to mechanically support the heat sink element.

14 Claims, 9 Drawing Sheets

1000

1010 Heat a support jacket to induce thermal expansion of a support structure of the support jacket, the support structure defining an aperture extending along an axis oriented along a generally longitudinal direction of the support structure.

1020 Insert a first tube into the aperture defined by the support structure of the support jacket, the first tube having opposing first and second ends and a first body structure between the opposing first and second ends, the first body structure defining an approximately cylindrical tube structure.

1030 Insert a second tube into the aperture defined by the support structure of the support jacket, the second tube having opposing first and second ends and a second body structure between the opposing first and second ends, the second body structure defining an approximately cylindrical tube structure.

1040 Cool the support jacket to induce thermal contraction of the support structure of the support jacket, the support structure locking in place the first tube and the second tube in a substantially concentric configuration.

FIG. 10

SAMPLE PREPARATION ASSEMBLY

CROSS-REFERENCE TO RELATED APPLICATIONS

The following patent applications are incorporated by reference in their entireties:

| Title | Filing Date | Ser. No. |
|---|---|---|
| Torch Assembly | May 12, 2010 | 12/778,490 |

FIELD

The present invention relates generally to laboratory instrumentation, particularly to a sample preparation assembly, and more specifically, to a sample preparation assembly for use with laboratory instrumentation for chemical analysis.

BACKGROUND

Analytical equipment, including mass spectrometers (MS) and atomic emission spectrometers (AES), are utilized for detecting trace elements of species in samples. Inductively Coupled Plasma MS (ICP-MS) and Inductively Coupled Plasma AES (ICP-AES) are two common analytical tools used by laboratories for the determination of trace element concentrations in samples. Such sample analysis systems may employ a sample introduction system for conditioning a sample prior to introduction into the analytical equipment. A sample may be introduced to the analytical equipment by the sample introduction system, whereby a concentration of elements and a ratio of isotopes may be detected by the analytical equipment.

SUMMARY

A sample preparation assembly includes a torch configured for use with an inductively coupled plasma spectroscopy instrument. The torch includes at least two approximately cylindrical tubes arranged substantially concentrically. The at least two approximately cylindrical tubes include a first outer tube and a second inner tube with a gap formed between the first outer tube and the second inner tube. The first outer tube and the second inner tube are each coupled to a mounting element configured for securing in place the first outer tube and the second inner tube. The sample preparation assembly also includes an injector configured for use with the inductively coupled plasma spectroscopy instrument. The injector includes an injection nozzle and a spray chamber. An exit of the spray chamber leads to the injection nozzle. The injection nozzle is positioned at least substantially within the second inner tube when the spray chamber is positioned adjacent the mounting element of the torch. The sample preparation assembly further includes a heat sink element. The heat sink element includes a securing element. The securing element is configured to mate with the mounting element of the torch to mechanically support the heat sink element. The securing element defines at least one aperture through which an inlet of the spray chamber passes.

A system includes an analytic instrument configured for chemical analysis of a sample. The system also includes a sample preparation assembly. The sample preparation assembly includes a torch configured to couple to an inlet of the analytic instrument. The torch includes at least two approximately cylindrical tubes arranged substantially concentrically. The at least two approximately cylindrical tubes include a first outer tube and a second inner tube with a gap formed between the first outer tube and the second inner tube. The first outer tube and the second inner tube are each coupled to a mounting element configured for securing in place the first outer tube and the second inner tube. The sample preparation assembly also includes an injector configured to introduce the sample to the analytic instrument. The injector includes an injection nozzle and a spray chamber. An exit of the spray chamber leads to the injection nozzle. The injection nozzle is positioned at least substantially within the second inner tube when the spray chamber is positioned adjacent the mounting element of the torch. The sample preparation assembly further includes a heat sink element. The heat sink element includes a securing element. The securing element is configured to mate with the mounting element of the torch to mechanically support the heat sink element. The securing element defines at least one aperture through which an inlet of the spray chamber passes.

A method of assembling a sample preparation device includes arranging at least two approximately cylindrical tubes of a torch substantially concentrically. The at least two approximately cylindrical tubes include a first outer tube and a second inner tube. The method also includes forming a gap between the first outer tube and the second inner tube. The method further includes coupling each of the first outer tube and the second inner tube to a mounting element configured for securing the relative positioning of the first outer tube and the second inner tube. The method additionally includes positioning a spray chamber of an injector adjacent the mounting element of the torch. The method still further includes positioning an injection nozzle of an injector at least substantially within the second inner tube. The method also includes mating a securing element of a heat sink with the mounting element of the torch to mechanically support the heat sink element. The method additionally includes defining at least one aperture in at least one of the mounting element or the securing element through which an inlet of the spray chamber passes.

It is to be understood that both the foregoing general description and the following detailed description are exemplary and explanatory only and are not necessarily restrictive as claimed. The accompanying drawings, which are incorporated in and constitute a part of the specification, illustrate an embodiment and together with the general description, serve to explain the principles of the disclosure.

BRIEF DESCRIPTION OF THE DRAWINGS

The numerous advantages of the disclosure may be better understood by those skilled in the art by reference to the accompanying figures in which:

FIG. 10 is a flow chart of a method of assembling a torch assembly.

DETAILED DESCRIPTION

Reference will now be made in detail to the presently preferred embodiments of the disclosure, examples of which are illustrated in the accompanying drawings.

Figure 1:
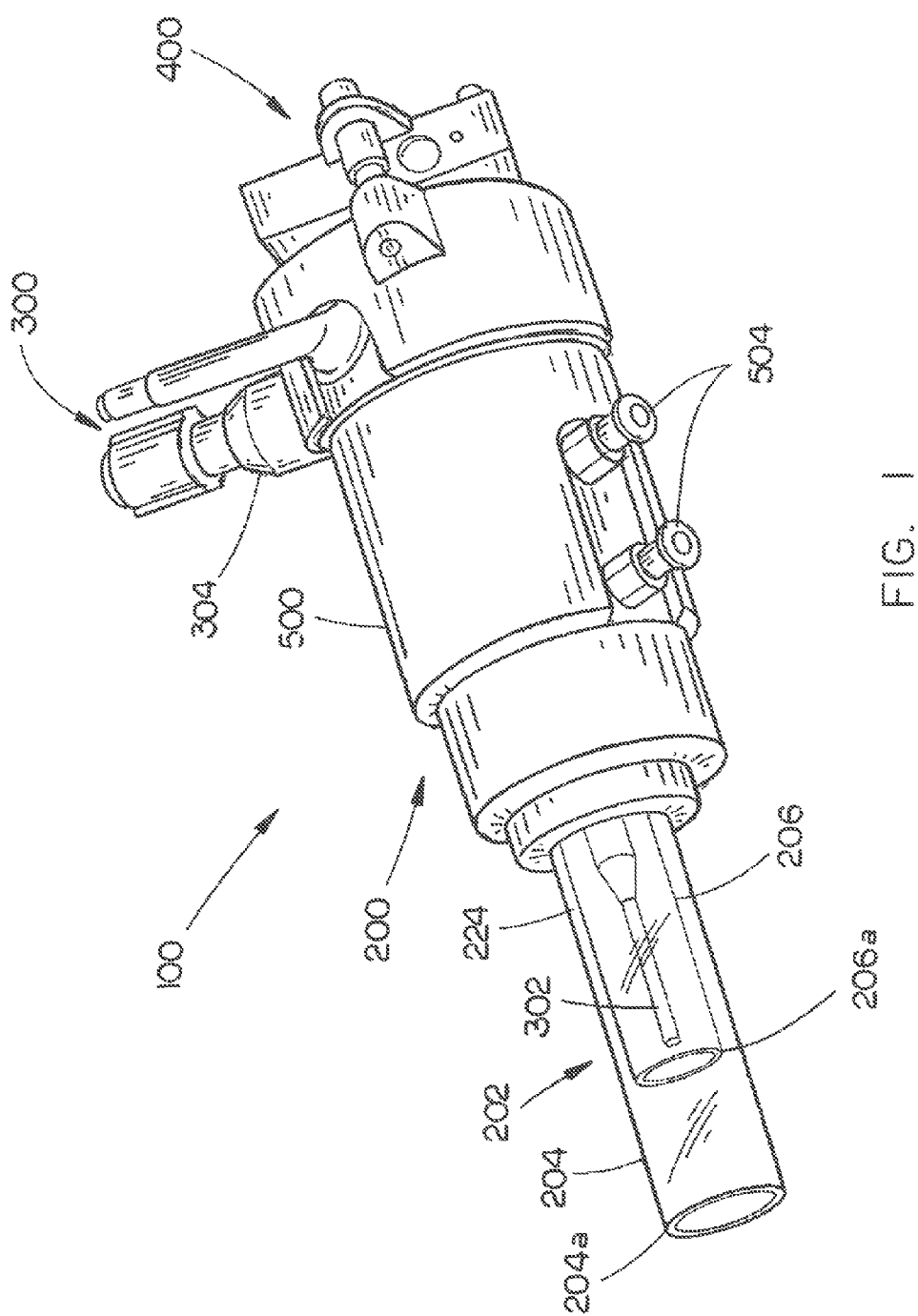
FIG. 1 is an isometric view of an embodiment of a sample preparation assembly configured for use with analytic equipment in the chemical analysis of a sample.
Figure 2:
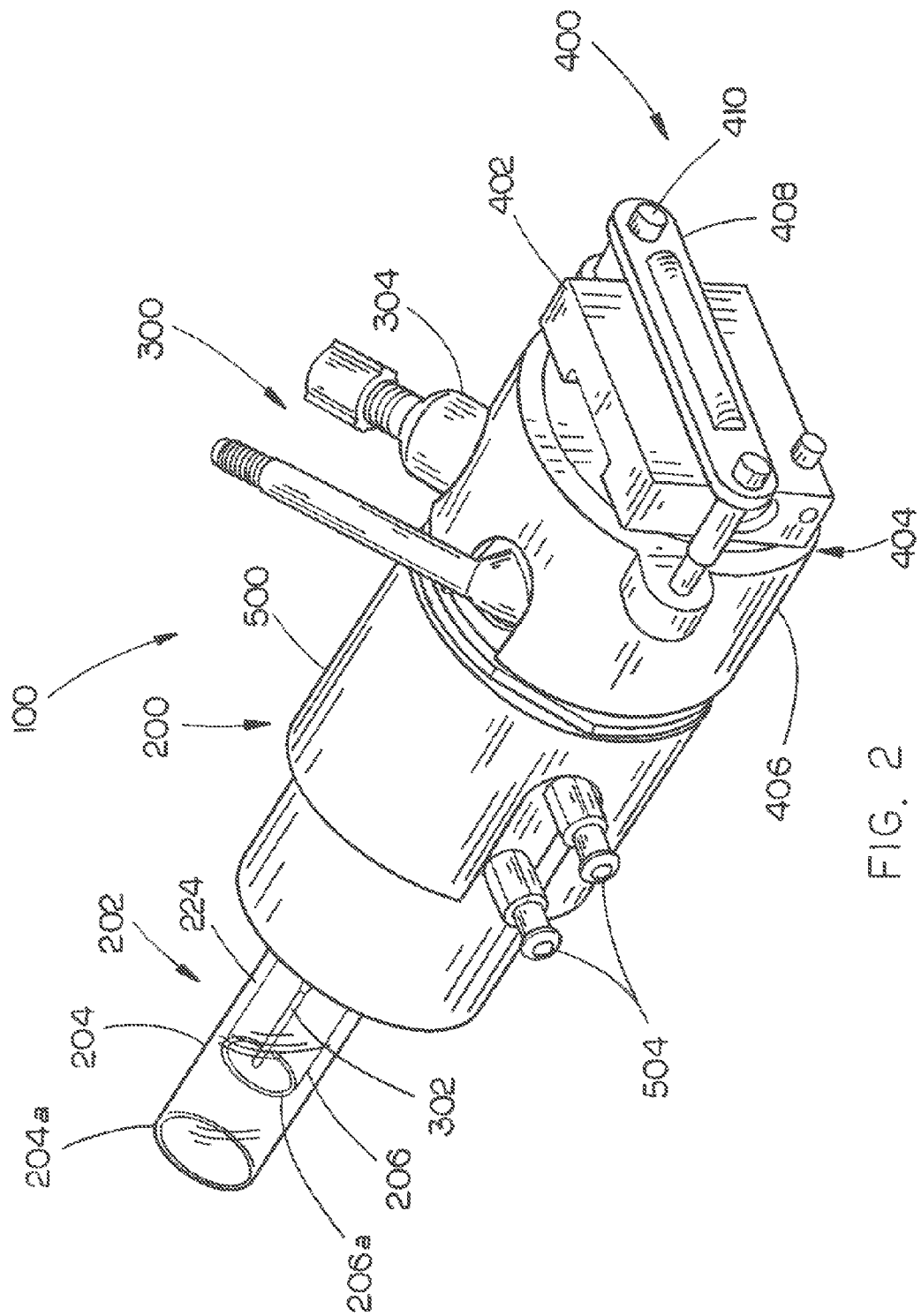
FIG. 2 is another isometric view of the sample preparation assembly of FIG. 1.
Figure 3:
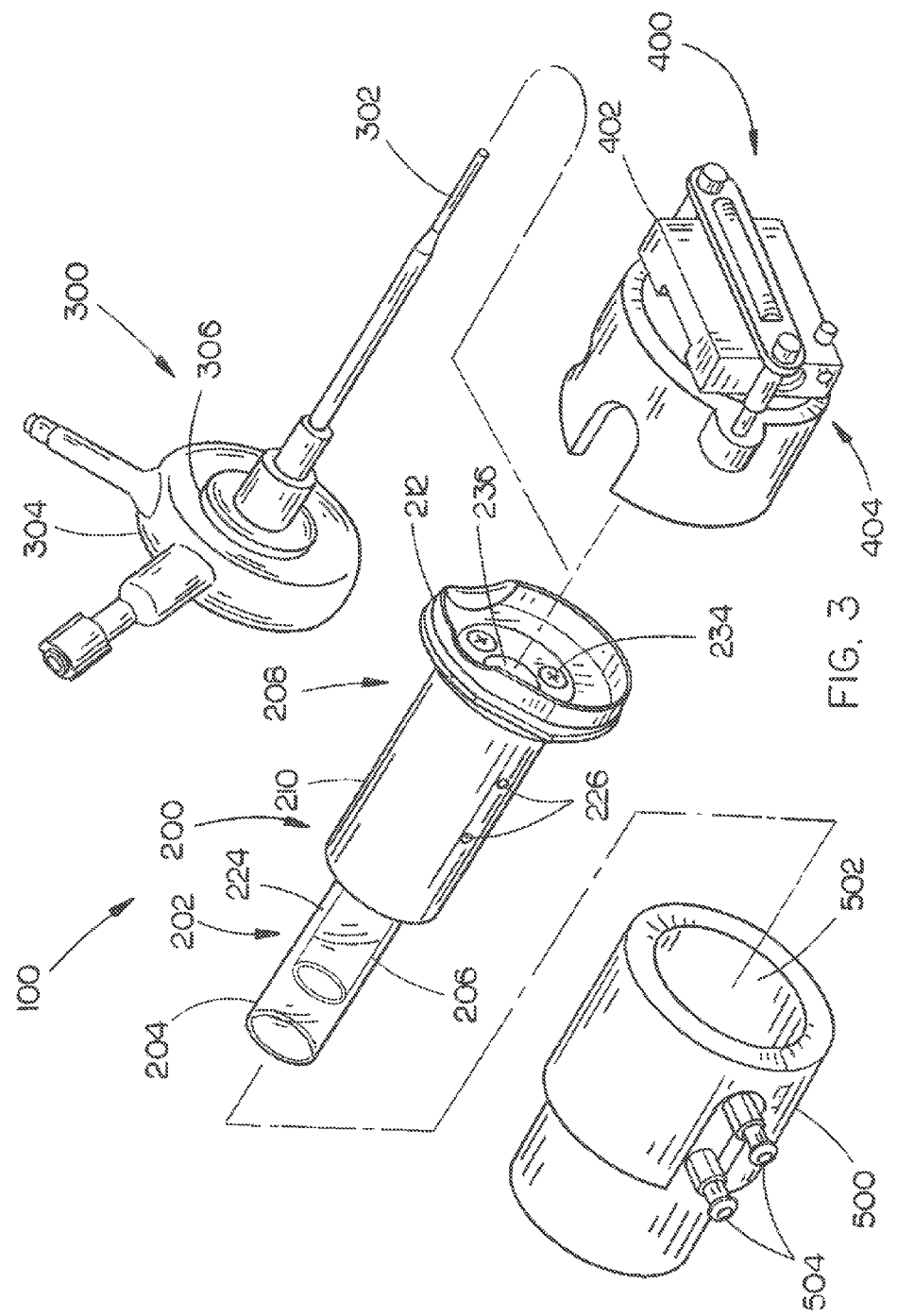
FIG. 3 is a partially exploded isometric view of the sample preparation assembly of FIG. 1.
Figure 4:
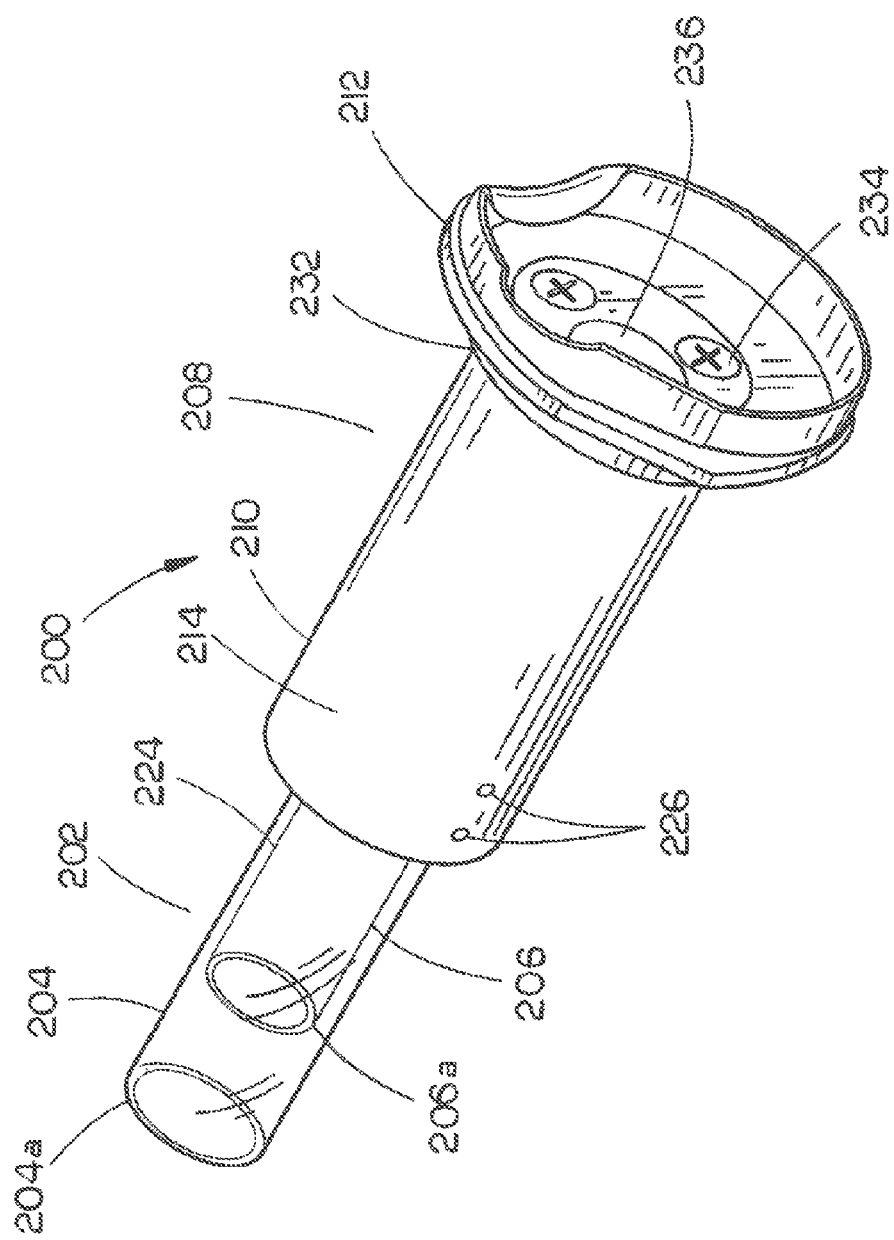
FIG. 4 is an isometric view of a torch assembly of the sample preparation assembly of FIG. 1.

Referring to FIGS. 1-3, an embodiment of a sample preparation assembly 100 is shown. The sample preparation assembly 100 may generally include at least three portions: a torch assembly 200, an injector 300, and a heat sink element 400. The torch assembly 200, the injector 300, and the heat sink element 400 may generally be coupled together to form the sample preparation assembly 100, which in turn may be coupled with analytic equipment configured for chemical analysis of a sample. For example, in one embodiment, the sample preparation assembly 100 may be included as at least a portion of inductively coupled plasma (ICP) equipment, such as for use in chemical analysis.

The torch assembly 200 may be configured for use with an ICP spectroscopy instrument. As seen in FIGS. 1-8, the torch assembly 200 may include at least two approximately cylindrical tubes 202 arranged substantially concentrically. The at least two approximately cylindrical tubes 202 may include a first outer tube 204 and a second inner tube 206. The first outer tube 204 may include opposing first and second ends 204a, 204b, and a first body structure 204c between the opposing first and second ends 204a, 204b. The second inner tube 206 may include opposing first and second ends 206a, 206b, and a second body structure 206c between the opposing first and second ends 206a, 206b. The first outer tube 204 and the second inner tube 206 may each be coupled to a mounting element 208. The mounting element 208 may include a support jacket 210 and a mounting bracket 212 coupled to an end of support jacket 210. The mounting element 208 may be configured for securing in place the first outer tube 204 and the second inner tube 206, such as in the substantially concentric configuration.

Figure 5:
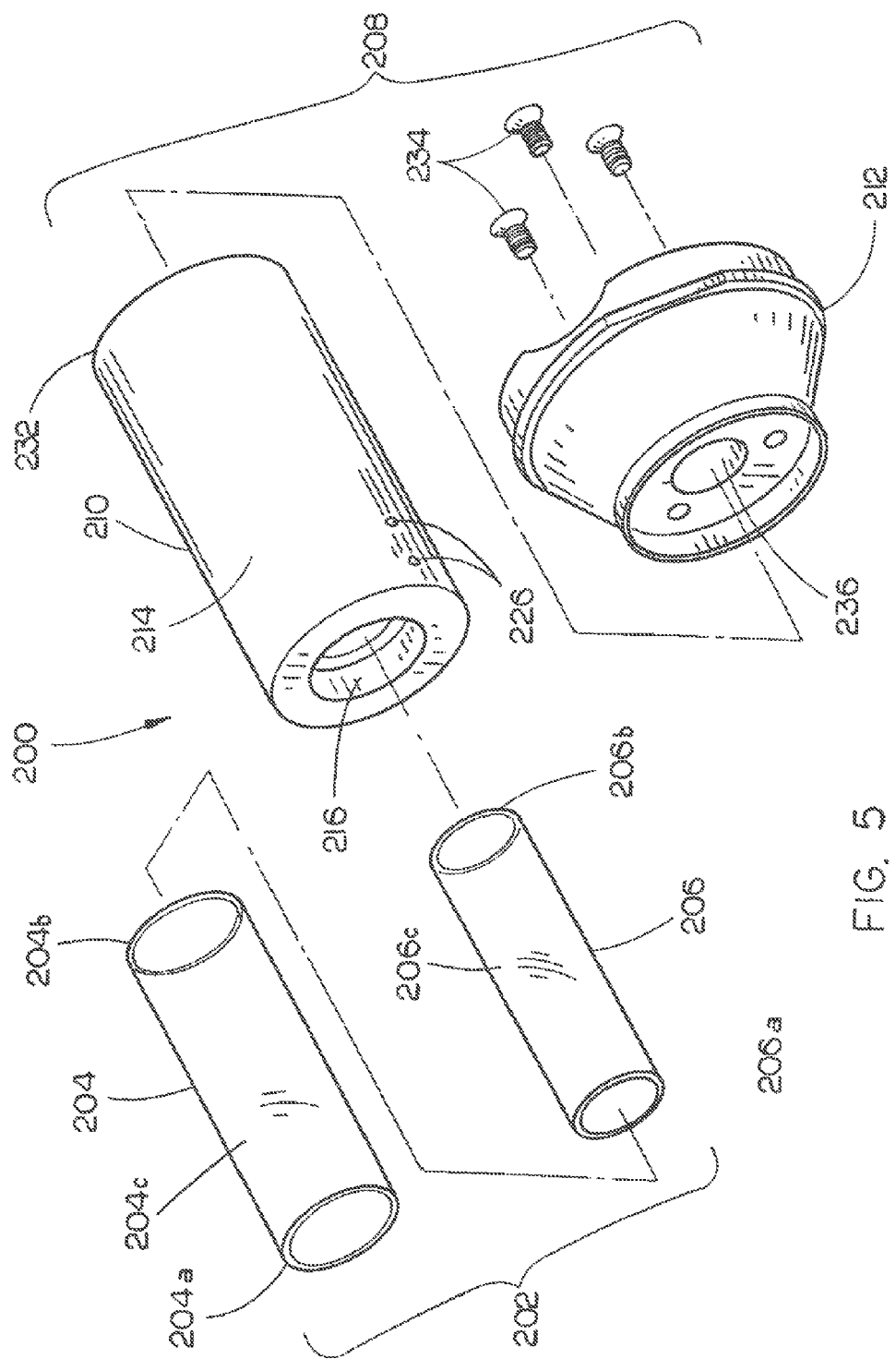
FIG. 5 is an exploded isometric view of the torch assembly of FIG. 4.
Figure 6:
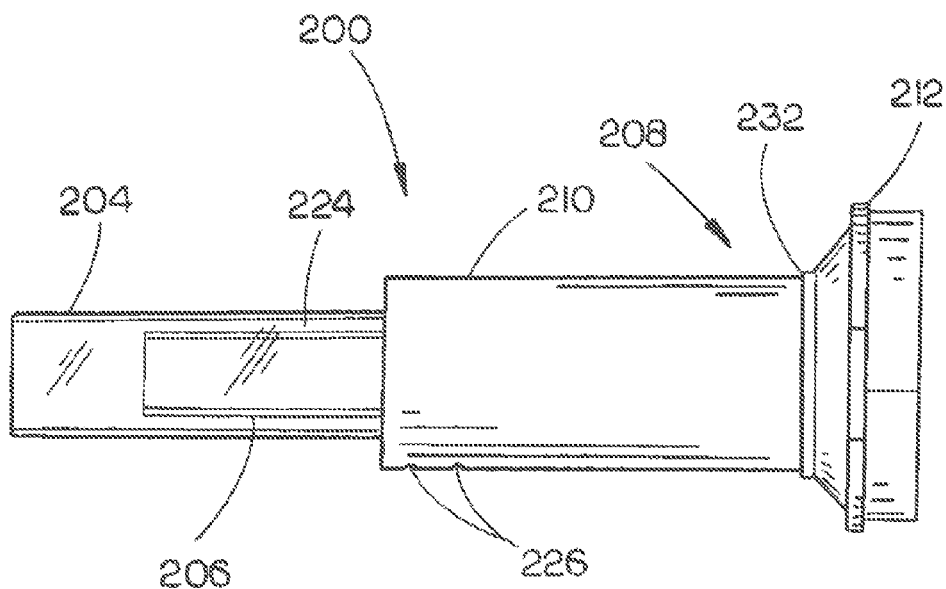
FIG. 6 is a side elevation view of the torch assembly of FIG. 4.
Figure 7:
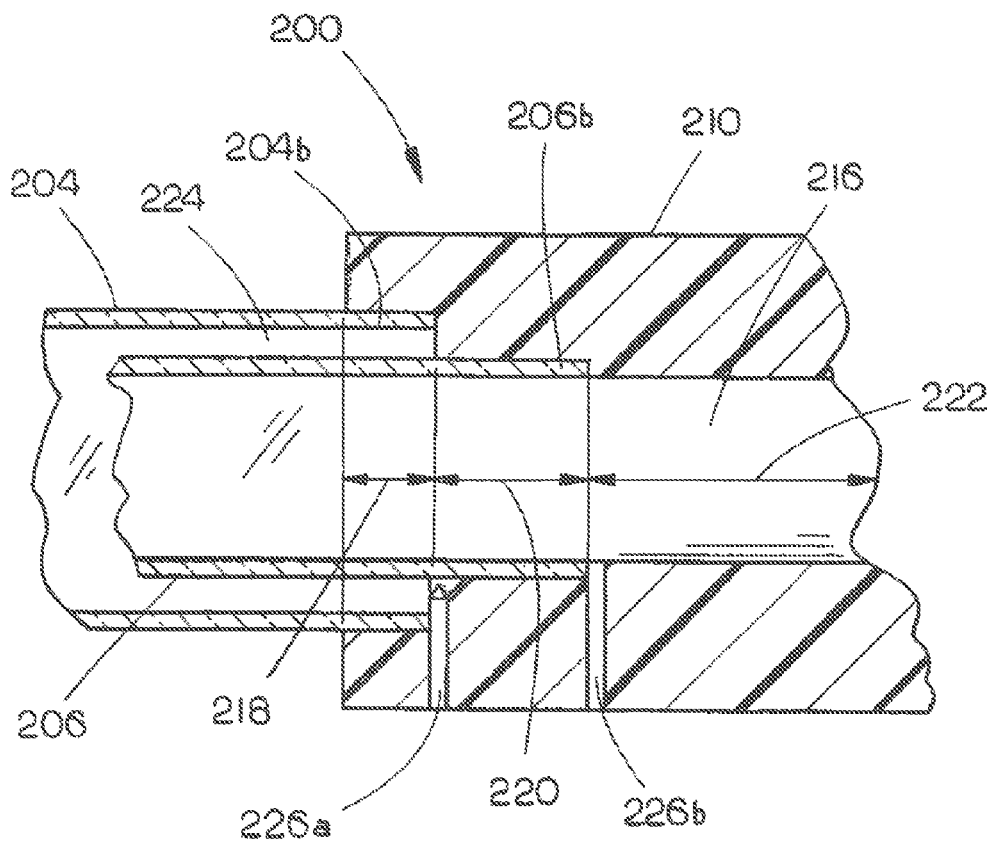
FIG. 7 is a partial cross-sectional view of the torch assembly of FIG. 4.
Figure 8:
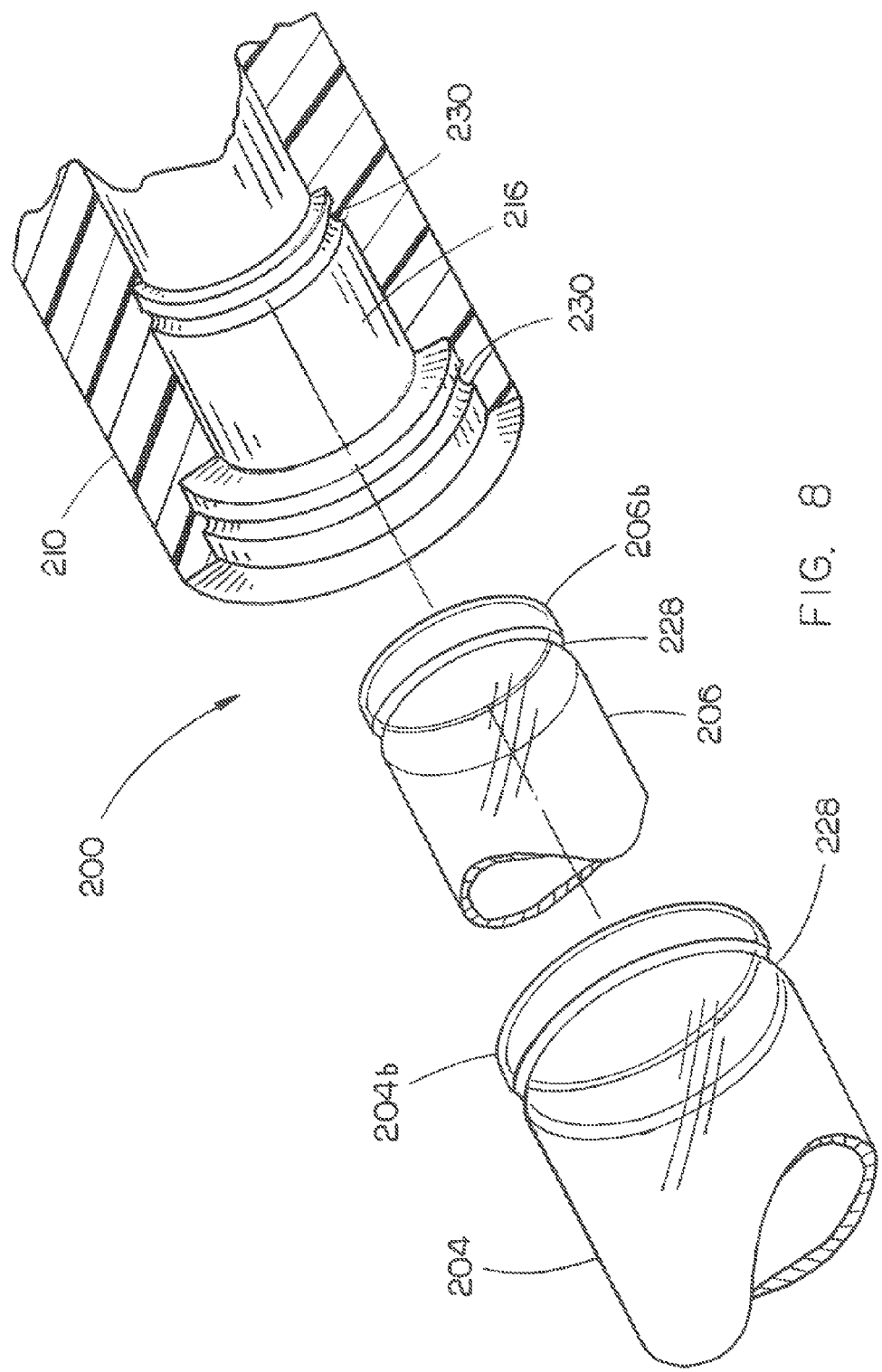
FIG. 8 is a partial isometric exploded cross-sectional view of an embodiment of a torch assembly.

The support jacket 210 may include a support structure 214, which may form the body of the support jacket 210. The support structure 214 may comprise a structural material (e.g., a plastic or plastic composite) that may be configured for thermal expansion and thermal contraction, as will be discussed further below. The support structure 214 may also define an aperture 216 extending along an axis oriented along a generally longitudinal direction of the support structure 214 (FIGS. 5, 7, and 8). The aperture 216 may generally be configured for receiving each of the first outer tube 204 and the second inner tube 206. For instance, the second end 204b of the first outer tube 204 and the second end 206b of the second inner tube 206 may be configured for insertion into the aperture 216. In one embodiment, the second end 204b of the first outer tube 204 and the second end 206b of the second inner tube 206 each have a cross sectional area relative to the axis of the support structure 214 that is less than the cross sectional area of the aperture 216. For instance, when the second end 204b of the first outer tube 204 has a circular cross sectional area (e.g., when the first outer tube 204 has a cylindrical shape), a smaller cross sectional area than the sectional area of the aperture 216 may permit insertion of the second end 204b into the aperture 216.

In another embodiment, the cross sectional area of the aperture 216 relative to the axis of the support structure 214 varies along the axis, such as in a generally longitudinal direction of the support structure 214. In one specific embodiment, the cross sectional area decreases (i.e., the amount of empty space of the aperture decreases) in a direction from an end of the aperture 216 of the support structure 214 into which the first outer tube 204 and the second inner tube 206 are inserted to an end of the aperture 216 opposing the end of the aperture 216 of the support structure 214 into which the first outer tube 204 and the second inner tube 206 are inserted. For instance, as shown in FIG. 7, the aperture 216 of the support structure 214 may have a first cross sectional area for a first portion 218 of the support structure 214 and a second cross sectional area for a second portion 220 of the support structure 214. The first portion 218 and the second portion 220 may each extend in a generally longitudinal direction of the support structure 214.

The cross sectional area of the second end 204b of the first outer tube 204 may be at least substantially similar to the first cross sectional area for the first portion 218 and greater than the second cross sectional area for the second portion 220. In this case, the second end 204b of the first outer tube 204 may be inserted into the aperture 216 up to the beginning of the second portion, where the support structure 214 may substantially impede or prevent progress of the first outer tube 204 further into the aperture 216. The cross sectional area of the second end 206b of the second inner tube 206 may be less than the first cross sectional area for the first portion 218 and at least substantially similar to the second cross sectional area for the second portion 220. In this case, the second end 206b of the second inner tube 206 may be inserted into the aperture 216 beyond the first portion 218 and into the second portion 220.

Where cross sectional areas are defined as "at least substantially similar to," it may be appreciated that "at least substantially similar" may include ranges of cross sectional areas which may be slightly greater than or slightly less than. For instance, the support structure 214 of the support jacket 210 may comprise a structural material (e.g., a plastic or plastic composite) that may be configured for thermal expansion and thermal contraction. Thus, the cross sectional area of the aperture 216 defined by the support structure 214 may vary depending on the temperature of the structural material. When heated, the structural material of the support structure 214 may expand, causing the aperture 216 to have a proportionately larger cross sectional area. When cooled from the heated temperature, the structural material of the support structure 214 may then contract, causing the aperture 216 to have a relatively smaller cross sectional area than when the structural material is heated. Thus, even if a substantially similar cross sectional area of the second end 204b of the first outer tube 204 is slightly larger than the first cross sectional area for the first portion 218, the first outer tube 204 may be inserted into the aperture 216 when the structural material of the support structure 214 is heated. After the first outer tube 204 is at least partially inserted into the aperture 216, the structural material of the support structure 214 may be subsequently cooled, which may cause the first portion 218 of the support structure 214 to contract around the at least partially-inserted portion of the first outer tube 204, locking the first outer tube 204 in place relative to the support structure 214. Similarly, the second inner tube 206 may be inserted into the aperture 216 when the support structure 214 is heated and then subsequently cooled, which may cause the second portion 220 of the support structure 214 to contact the second inner tube 206, locking the second outer tube 206 in place relative to the support structure 214.

Alternatively, it may be appreciated that a substantially similar cross sectional area of the second end 204b of the first outer tube 204 may be used which may be slightly smaller than the first cross sectional area for the first portion 218 when the support structure 214 is relatively cool. In this case, insertion of the first outer tube 204 into the aperture 216 may be enabled even when the support structure 214 is in a non-expanded state. The first outer tube 204 may be held place relative to the support structure 214 by selecting substantially similar cross sectional areas, which may allow frictional forces and the like to lock in place the first outer tube 204 relative to the support structure 214.

In another embodiment, the aperture 216 of the support structure 214 may have a third cross sectional area for a third portion 222 of the support structure 214. Similar to the first portion 218 and the second portion 220, the third portion 22 may also extend in a generally longitudinal direction of the support structure 214. In the embodiment shown in FIG. 7, the third cross sectional area of the third portion 22 is less than the second cross sectional area of the second portion 220, which in turn is less than the first cross sectional area of the first portion 218. When the aperture 216 of the support structure 214 has a third cross sectional area that is less than the second cross sectional area of the second portion 220, the second inner tube 206 may be inserted into the aperture 216 up to the beginning of the third portion, where the support structure 214 may substantially impede or prevent progress of the second inner tube 206 further into the aperture 216.

When the first outer tube 204 and the second inner tube 206 are arranged substantially concentrically in the support jacket 210, a gap 224 may be formed between the first outer tube 204 and the second inner tube 206, as seen in FIGS. 1-4, 6, and 7. The gap 224 may allow the flow of fluids, such as gases, liquids, and plasma, between first outer tube 204 and the second inner tube 206, such as to enable functioning of a torch in inductively coupled plasma technology, as will be appreciated by those of skill in the art.

The support structure 214 of the support jacket 210 may also define at least one fluid port 226 on a side of the support jacket 210. The fluid port 226 may be oriented on an axis that is approximately perpendicular to the axis oriented along the generally longitudinal direction of the support structure 214. For instance, in the embodiment shown in FIG. 7, fluid ports 226a, 226b are substantially perpendicular to the aperture 216 defined by the support structure 214. Fluid port 226 may permit the introduction and/or removal of fluids from the torch assembly 200, such as for proper ICP functionality. In one embodiment, such as that shown in FIG. 7, the first portion 218 of the support structure 214 may begin at an outer edge of fluid port 226a and may end at the end of the aperture 216 of the support structure 214 into which the first outer tube 204 and the second inner tube 206 are inserted. The second portion 220 of the support structure 214 may begin at an outer edge of another fluid port 226b and may end at an outer edge of fluid port 226a. Such a configuration may permit fluid flow in the gap 224 to flow into and/or out of fluid port 226a without affecting the fluid flow into and/or out of fluid port 226b. In another embodiment, the third portion 222 of the support structure 214 may begin at an end of the support structure 214 opposite of the end into which the first outer tube 204 and the second inner tube 206 are inserted and may end at an edge of the fluid inlet 226b.

In a further embodiment shown in FIG. 8, the torch assembly 200 may include a further securing or locking mechanism, whereby the first outer tube 204 and the second inner tube 206 are secured in place relative to the support jacket 210. In this embodiment, the first outer tube 204 and/or the second inner tube 206 may define a groove 228 located on at least a portion of the first body structure 204c and/or the second body structure 206c. The support structure 214 may include a corresponding raised portion 230 configured to align with the groove 228 of the first outer tube 204 and/or the second inner tube 206. In one specific embodiment, the support structure 214 includes a raised portion 230 on the first portion 218 which corresponds with the groove 228 on the first outer tube 204, and includes a raised portion 230 on the second portion 220 which corresponds with the groove 228 on the second inner tube 206. At least a portion of the raised portion 230 may interact with the groove 228 when the first outer tube 204 and/or the second inner tube 206 is inserted into the aperture 216, in order to hold in place the first outer tube 204 and/or the second inner tube 206 relative to the support jacket 210.

The aperture 216 may extend through the entirety of the longitudinal direction of the support structure 214, such that an opening is present at an end 232 (FIGS. 4-6) of the support structure 214 opposite the end into which the first outer tube 204 and the second inner tube 206 are inserted. The mounting bracket 212 of the torch assembly 200 may be coupled with the support jacket 210 at the end 232 of the support structure 214. For example, the mounting bracket 212 may be secured to the support jacket 210 with fasteners 234. The mounting bracket 212 may define an aperture 236, which may substantially align with the aperture 216 of the support structure 214 when the mounting bracket 212 is coupled with the end 232 of the support jacket 210. Alignment of apertures 216 and 236 may allow for insertion of other portions of the sample preparation assembly 100, such as portions of injector 300, into the torch assembly 200, as will be discussed further below. The mounting bracket 212 may further be configured to provide structural support to the sample preparation assembly 100 when coupling together portions of the sample preparation assembly 100 including the torch assembly 200, the injector 300, and the heat sink element 400.

The injector 300 may generally be configured use with an ICP spectroscopy instrument. The injector 300 may include an injection nozzle 302 and a spray chamber 304. The injection nozzle 302 may be coupled with the spray chamber 304, such that an exit 306 of the spray chamber 304 may lead to the injection nozzle 302. The injector 300 may be configured to couple with and adjacent to the torch assembly 200, and in a particular embodiment, the injector 300 is configured to couple between the torch assembly 200 and the heat sink element 400. As seen in FIGS. 1 and 2, the injection nozzle 302 may be positioned at least substantially within the second inner tube 206 when the spray chamber 304 is positioned adjacent the mounting bracket 212 of the torch assembly 200. For instance, the mounting bracket 212 may be configured to at least partially enclose a portion of the spray chamber 304 when the injection nozzle 302 is fully inserted into the aperture 216 defined by the support structure 214. When the first outer tube 204 and the second inner tube 206 are in the substantially concentric configuration coupled with the support structure 214, the injector 300 may be placed adjacent the torch assembly 200, whereby the injection nozzle 302 may be fully inserted into the aperture 216, placing the injection nozzle 302 within the interior of the second inner tube 206. In a particular embodiment, the spray chamber 304 is a cyclonic spray chamber for use with an ICP spectroscopy instrument.

The heat sink element 400 of the sample preparation assembly 100 may generally be configured to improve the quality of data measured by the ICP spectroscopy instrument. For instance, in one specific embodiment, the heat sink element 400 may be a Peltier cooling device configured to reduce the ambient temperature of the spray chamber 304 to reduce the partial pressure of water vapor, such as to avoid drift/interference in an analysis of a chemical sample. The heat sink element 400 may include a heat sink portion 402 and a securing element 404. In one embodiment, the heat sink portion 402 is a fluid-cooled heat sink, which may utilize a flow of fluid and/or a volume of fluid as a heat transfer agent to control the temperature of the heat sink element 400 and of the sample to be introduced by the sample preparation assembly 100 into the ICP spectroscopy instrument. In another embodiment, the heat sink element 400 may include and/or be replaced with a heating element configured to control the temperature of the spray chamber 304, such as by increasing the temperature.

The securing element 404 may be configured to mate with the mounting element 208 of the torch assembly 200 to mechanically support the heat sink element 400. For instance, the securing element 404 may couple with the mounting bracket 208 of the torch assembly 200. In such an instance, the mounting bracket 208 and/or the securing element 404 may at least partially surround the spray chamber 304, thereby coupling the spray chamber 304 to the sample preparation assembly 100. In one specific embodiment, the securing element 404 includes a securing cap 406 and a securing bracket 408. The securing cap 406 may be configured to at least partially surround the spray chamber 304 and to couple with the mounting bracket 212 of the torch assembly 200. The securing cap 406 may define an aperture or a recess through which an inlet and/or outlet of the spray chamber 304 may pass, as seen in FIGS. 1-3. The securing bracket 408 may be coupled with the securing cap 406 via pins/fasteners 410. The heat sink portion 402 may be located between the securing cap 406 and the securing bracket 408 and held in place by the coupling of the securing bracket 408 to the securing cap 406 by pins/fasteners 410.

The sample preparation assembly 100 may further include a cover element 500. The cover element 500 may be configured to at least partially cover the torch assembly 200, as seen in FIGS. 1 and 2. The cover element 500 may mate with the mounting bracket 212 at an end of the mounting bracket 212 opposite the securing element 404 of the heat sink element 400 when the heat sink element 400 is coupled with the torch assembly 200. In the embodiment shown in FIG. 3, the cover element 500 defines an aperture 502 extending through the cover element 500 in a generally longitudinal direction. The aperture 502 may be configured such that the support jacket 210 of the torch assembly 200 may be inserted into the aperture 502 in order for the cover element 500 to at least partially cover the support jacket 210, as seen in FIGS. 1 and 2. The cover element 500 may also include at least one inlet 504 through which fluid may substantially pass. The at least one inlet 504 may be located on a side of the cover element 500 configured to substantially overlay with fluid port 226 defined by the support structure 214 when the cover element 500 is mated with the mounting bracket 212. A hose or tube may be coupled with the at least one inlet 504, such as to transport fluid to/from the torch assembly 200 via the cover element 500.

It is contemplated that the present disclosure provides a sample preparation assembly and/or a torch assembly that may be readily manufacturable via machine processing. For instance, the first outer tube 204 and the second inner tube 206 may be of an approximately equivalent length and be similar cylindrical-shaped tubes. By utilizing a support jacket 210 into which the first outer tube 204 and the second inner tube 206 are inserted and secured, the torch assembly 200 may be readily manufacturable via machine processing, while still maintaining tolerances sufficient to enable functioning ICP capabilities.

Figure 9:
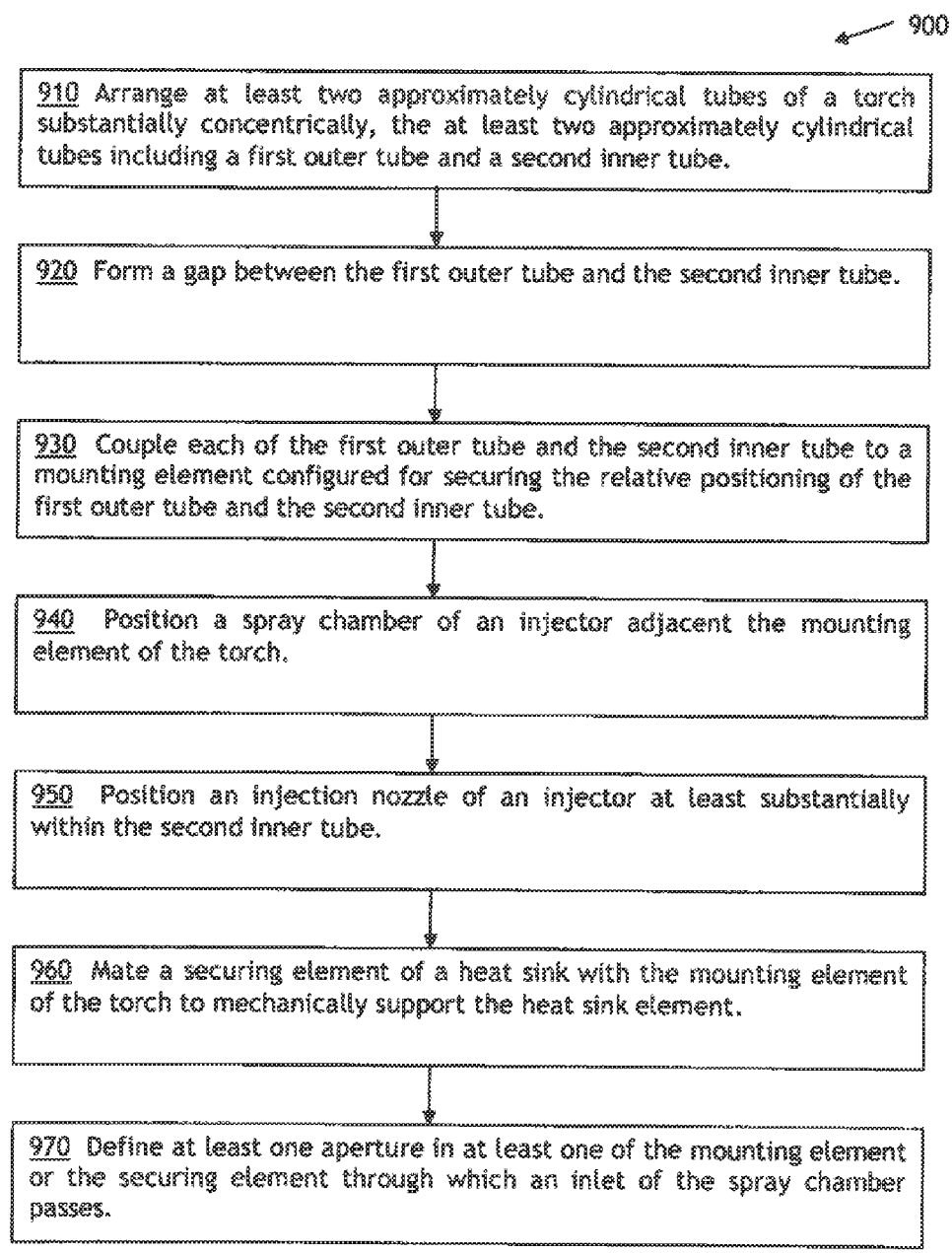
FIG. 9 is a flow chart of a method of assembling a sample preparation device.

Referring now to FIG. 9, a flow chart of a method 900 of assembling a sample preparation device is shown. The method 900 may include arranging at least two approximately cylindrical tubes of a torch substantially concentrically 910. The at least two approximately cylindrical tubes may include a first outer tube and a second inner tube. The method 900 may include forming a gap between the first outer tube and the second inner tube 920. The method 900 may include coupling each of the first outer tube and the second inner tube to a mounting element configured for securing the relative positioning of the first outer tube and the second inner tube 930. The method 900 may include positioning a spray chamber of an injector adjacent the mounting element of the torch 940. The method 900 may include positioning an injection nozzle of an injector at least substantially within the second inner tube 950. The method 900 may include mating a securing element of a heat sink with the mounting element of the torch to mechanically support the heat sink element 960. The method 900 may include defining at least one aperture in at least one of the mounting element or the securing element through which an inlet of the spray chamber passes 970.

Step 940 of method 900 may include positioning a cyclonic spray chamber of an injector adjacent the mounting element of the torch. Method 900 may further include mating a cover element with the mounting element at an end of the mounting element opposite the securing element of the heat sink element. The step of mating a cover element with the mounting element at an end of the mounting element opposite the securing element of the heat sink element may also include mating a cover element including at least one inlet through which a fluid may substantially pass with the mounting element at an end of the mounting element opposite the securing element of the heat sink element. Method 900 may further include at least substantially overlaying the at least one inlet with an aperture defined by the mounting element on a surface of a side of the mounting element when the cover element is mated with the mounting element. Method 900 may further include at least substantially enclosing the spray chamber with at least one of the mounting element or the securing element when the securing element is mated with the mounting element.

Referring now to FIG. 10, a flow chart of a method 1000 of assembling a torch assembly is shown. The method 1000 may include heating a support jacket to induce thermal expansion of a support structure of the support jacket 1010. The support structure may define an aperture extending along an axis oriented along a generally longitudinal direction of the support structure. The method 1000 may include inserting a first tube into the aperture defined by the support structure of the support jacket 1020. The first tube may have opposing first and second ends and a first body structure between the opposing first and second ends. The first body structure may define an approximately cylindrical tube structure. The method 1000 may include inserting a second tube into the aperture defined by the support structure of the support jacket 1030. The second tube may have opposing first and second ends and a second body structure between the opposing first and second ends. The second body structure may define an approximately cylindrical tube structure. The method 1000 may include cooling the support jacket to induce thermal contraction of the support structure of the support jacket 1040. The support structure may lock in place the first tube and the second tube in a substantially concentric configuration.

In the present disclosure, the methods disclosed may be implemented as sets of instructions or software readable by a device. Further, it is understood that the specific order or hierarchy of steps in the methods disclosed are examples of exemplary approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

It is believed that the present disclosure and many of its attendant advantages will be understood by the foregoing description, and it will be apparent that various changes may be made in the form, construction and arrangement of the components thereof without departing from the scope and spirit of the disclosure or without sacrificing all of its material advantages. The form herein before described being merely an explanatory embodiment thereof, it is the intention of the following claims to encompass and include such changes.

What is claimed is:

1. A sample preparation assembly, comprising:
    a torch configured for use with an inductively coupled plasma spectroscopy instrument, the torch including at least two approximately cylindrical tubes arranged substantially concentrically, the at least two approximately cylindrical tubes including a first outer tube and a second inner tube with a gap formed between the first outer tube and the second inner tube, the first outer tube and the second inner tube each coupled to a mounting element configured for securing in place the first outer tube and the second inner tube;
    an injector configured for use with the inductively coupled plasma spectroscopy instrument, the injector including an injection nozzle and a spray chamber, an exit of the spray chamber leading to the injection nozzle, the injection nozzle positioned at least substantially within the second inner tube when the spray chamber is positioned adjacent the mounting element of the torch; and
    a heat sink element, the heat sink element including a securing element, the securing element configured to mate with the mounting element of the torch to mechanically support the heat sink element, at least one of the securing element or the mounting element defining at least one aperture through which an inlet of the spray chamber passes.

2. The sample preparation assembly of claim 1, wherein the spray chamber is a cyclonic spray chamber.

3. The sample preparation assembly of claim 1, further including:
    a cover element, the cover element configured to mate with the mounting element at an end of the mounting element opposite the securing element of the heat sink element.

4. The sample preparation assembly of claim 3, wherein the cover element includes at least one inlet through which a fluid may substantially pass.

5. The sample preparation assembly of claim 4, wherein the at least one inlet is located on a side of the cover element configured to substantially overlay with an aperture defined by the mounting element on a surface of a side of the mounting element when the cover element is mated with the mounting element.

6. The sample preparation assembly of claim 1, wherein the heat sink is a fluid-cooled heat sink.

7. The sample preparation assembly of claim 1, wherein at least one of the mounting element or the securing element is configured to at Least substantially enclose the spray chamber when the securing element is mated with the mounting element.

8. A system, comprising:
    an analytic instrument configured for chemical analysis of a sample; and
    a sample preparation assembly, the sample preparation assembly including:
        a torch configured to couple to an inlet of the analytic instrument, the torch including at least two approximately cylindrical tubes arranged substantially concentrically, the at least two approximately cylindrical tubes including a first outer tube and a second inner tube with a gap formed between the first outer tube and the second inner tube, the first outer tube and the second inner tube each coupled to a mounting element configured for securing in place the first outer tube and the second inner tube;
        an injector configured to introduce the sample to the analytic instrument, the injector including an injection nozzle and a spray chamber, an exit of the spray chamber leading to the injection nozzle, the injection nozzle positioned at least substantially within the second inner tube when the spray chamber is positioned adjacent the mounting element of the torch; and
        a heat sink element, the heat sink element including a securing element, the securing element configured to mate with the mounting element of the torch to mechanically support the heat sink element, at least one of the securing element or the mounting element defining at least one aperture through which an inlet of the spray chamber passes.

9. The system of claim 8, wherein the spray chamber is a cyclonic spray chamber.

10. The system of claim 8, further including:
    a cover element, the cover element configured to mate with the mounting element at an end of the mounting element opposite the securing element of the heat sink element.

11. The system of claim 10, wherein the cover element includes at least one inlet through which a fluid may substantially pass.

12. The system of claim 11, wherein the at least one inlet is located on a side of the cover element configured to substantially overlay with an aperture defined by the mounting element on a surface of a side of the mounting element when the cover element is mated with the mounting element.

13. The system of claim 8, wherein the heat sink is a fluid-cooled heat sink.

14. The system of claim 8, wherein at least one of the mounting element or the securing element is configured to at least substantially enclose the spray chamber when the securing element is mated with the mounting element.

* * * * *